(12) United States Patent
Mahn et al.

(10) Patent No.: US 9,576,353 B2
(45) Date of Patent: Feb. 21, 2017

(54) METHOD FOR VERIFYING THE RELATIVE POSITION OF BONE STRUCTURES

(75) Inventors: Florian Mahn, Schliersee (DE); Gerhard Kleinszig, Kirchheim (DE)

(73) Assignee: Brainlab AG, Munich (DE)

( * ) Notice: Subject to any disclaimer, the term of this patent is extended or adjusted under 35 U.S.C. 154(b) by 913 days.

(21) Appl. No.: 12/556,795

(22) Filed: Sep. 10, 2009

(65) Prior Publication Data
US 2010/0063420 A1 Mar. 11, 2010

Related U.S. Application Data

(60) Provisional application No. 61/119,756, filed on Dec. 4, 2008.

(30) Foreign Application Priority Data

Sep. 10, 2008 (EP) .................................. 08164087

(51) Int. Cl.
A61B 5/103 (2006.01)
A61B 5/117 (2016.01)
G06T 7/00 (2006.01)
A61B 19/00 (2006.01)

(52) U.S. Cl.
CPC .............. *G06T 7/0012* (2013.01); *A61B 19/50* (2013.01); *A61B 19/5244* (2013.01); *A61B 2019/502* (2013.01); *A61B 2019/505* (2013.01); *A61B 2019/507* (2013.01); *A61B 2019/5268* (2013.01); *A61B 2019/5289* (2013.01); *G06T 2207/10081* (2013.01); *G06T 2207/30008* (2013.01); *G06T 2207/30012* (2013.01)

(58) Field of Classification Search
CPC ................ A61B 19/50; A61B 19/5244; A61B 2019/502;A61B 2019/505; A61B 2019/507; A61B 2019/5268; A61B 2019/5289; G06T 2207/30008; G06T 2207/30012
USPC ........ 600/427, 429, 587, 594; 623/902, 908; 128/920, 922, 923; 382/128, 131
See application file for complete search history.

(56) References Cited

U.S. PATENT DOCUMENTS

| 5,291,537 A | 3/1994 | Mazess |
| 5,582,186 A | 12/1996 | Wiegand |
| 6,434,415 B1 * | 8/2002 | Foley et al. .................. 600/425 |

(Continued)

OTHER PUBLICATIONS

Benameur et al., "A Hierarchical Statistical Modeling Approach for the Unsupervised 3-D Biplanar Reconstruction of the Scoliotic Spine", IEEE Transactions on Biomedical Engineering, vol. 52, No. 12, Dec. 2005, pp. 2041-2057.

(Continued)

*Primary Examiner* — Devin Henson
(74) *Attorney, Agent, or Firm* — Tucker Ellis LLP (57) ABSTRACT

A method for verifying the position of at least two bone structures relative to each other, comprising the method steps of: recording a three-dimensional dataset which represents the bone structures; segmenting the three-dimensional dataset into segments, wherein each segment represents a bone structure and the segments exhibit a known relative position in the three-dimensional dataset; changing the virtual relative position of the segments, such that the virtual relative position of the segments matches the actual relative position of the bone structures; and verifying whether the virtual relative position of the segments matches a target position of the bone structures.

14 Claims, 6 Drawing Sheets

(56) References Cited

U.S. PATENT DOCUMENTS

| | | | |
|---|---|---|---|
| 2004/0215071 A1* | 10/2004 | Frank et al. | 600/407 |
| 2005/0119593 A1 | 6/2005 | Gallard et al. | |
| 2008/0132784 A1* | 6/2008 | Porat et al. | 600/426 |
| 2008/0287781 A1* | 11/2008 | Revie et al. | 600/426 |
| 2009/0087052 A1* | 4/2009 | Amiot et al. | 382/128 |
| 2010/0030232 A1* | 2/2010 | Zehavi et al. | 606/130 |

OTHER PUBLICATIONS

Benameur et al., "3D/2D registration and segmentation of scoliotic vertebrae using statistical models", Computerized Medical Imaging and Graphics, Pergamon Press, vol. 27, No. 5, Sep. 2003, pp. 321-337.

Dumas et al., "Validation of the relative 3D orientation of vertebrae reconstructed by bi-planar radiography", Medical Engineering & Physics, vol. 26, No. 5, Jun. 2004, pp. 415-422.

Gruescu et al., "Relative Rotation Angle Between Spinal Vertebrae Using Complex Shape Markers", Annals of the Oradea University, Fascicle of Management and Technological Engineering, [Online], <URL: http://imtuoradea.ro/auo.fmte/MECATRONICA_files/GRUESCU%20CORINA%201.pdf>, vol. VII, No. 30, May 2008, pp. 847-852.

Verdonck et al., "Computer Assisted Quantitative Analysis of Deformities of the Human Spine", Medical Image Computing and Computer-Assisted Intervention. MICCAI International Conference Proceedings, Jan. 1998, pp. 822-831.

Petit et al., "Estimation of 3D location and orientation of human vertebral facet joints from standing digital radiographs", Medical and Biological Engineering and Computing, vol. 36, No. 4, Jul. 1998, pp. 389-394.

Kang et al., A New Accurate and Precise 3-D Segmentation Method for Skeletal Structures in Volumetric CT Data, IEEE Transactions on Medical Imaging, vol. 22, No. 5 May 2003 pp. 586-598.

* cited by examiner

METHOD FOR VERIFYING THE RELATIVE POSITION OF BONE STRUCTURES

RELATED APPLICATION DATA

This application claims the priority of U.S. Provisional Application No. 61/119,756, filed on Dec. 4, 2008, which is hereby incorporated in its entirety by reference.

FIELD OF THE INVENTION

The present invention relates to a method for verifying the position of at least two bone structures, in particular at least two vertebrae of a spine, relative to each other.

BACKGROUND OF THE INVENTION

When performing an operation, it is often necessary to know the position of bone structures relative to each other. Bone structures include for example vertebrae of a spine or fragments of a bone. In the case of bone fractures, the correct position of the fragments is crucial for them to knit correctly. The position of vertebrae of a spine is important when implanting artificial intervertebral discs, implanting cages, stiffening two vertebrae (interbody fusion), inserting artificial facet joints or employing dynamic stabilization.

One option is to repeatedly produce 3D images during the operation. However, this is time-consuming, and the device necessary for it is obstructive in the operating environment. Another option is to provide each bone structure with a marking device and to detect the relative positions of the marked devices, for example via a 3D camera. This presupposes damage to the bone structure and requires an additional or enlarged opening in the body, through which a marker device can pass.

SUMMARY OF THE INVENTION

It is therefore the object of the present invention to provide a method for verifying the relative position of at least two bone structures which is quick, cost-effective and as little a burden on the patient as possible.

This object is solved by a method for verifying the position of at least two bone structures, in particular at least two vertebrae of a spine, relative to each other, comprising the method steps of: recording a three-dimensional dataset which represents the bone structures; segmenting the three-dimensional dataset into segments, wherein each segment represents a bone structure and the segments exhibit a known relative position in the three-dimensional dataset; changing the virtual relative position of the segments, such that the virtual relative position of the segments matches the actual relative position of the bone structures; verifying whether the virtual relative position of the segments matches a target position of the bone structures. The invention also relates to a program for performing the aforesaid method, a storage medium on which said program is stored, and a device on which the program is executed.

In the method in accordance with the invention for verifying the position of at least two bone structures (bones), in particular at least two vertebrae of a spine, relative to each other, a three-dimensional dataset is initially recorded which represents the bone structures (bones). The three-dimensional dataset is then segmented into segments, wherein each segment represents a bone structure (bone) and the segments exhibit a known relative position in the three-dimensional dataset. Where "bone structures" are mentioned here, this in particular encompasses the concept of the (individual) bones present in the anatomical body.

During segmenting, the entries in the three-dimensional dataset—for example, the voxels of a 3D image—are assigned to the segments. Entries in the three-dimensional dataset which cannot be attributed to a bone structure (for example, other tissue) are either not assigned to a segment or are distributed between the other segments. Each segment thus represents exactly one of the bone structures (exactly one bone). The three-dimensional dataset preferably contains the spatial density distribution of the bone structures.

In a subsequent step, the relative position of the segments is virtually changed into a virtual relative position, such that the virtual relative position of the segments matches the actual relative position of the bone structures. To this end, the segments are virtually shifted and/or rotated relative to each other. The virtual relative position of the segments then in particular deviates from the relative position which the segments assume in the three-dimensional dataset and corresponds to the relative position which the actual bone structures of the patient also assume with respect to each other. This is also referred to as registration. Lastly, a verification is made as to whether the virtual relative position of the segments matches a target position of the bone structures. The registration is used for this purpose. The actual position of the actual bone structure is determined using the registration, and a way is thus created to determine a deviation between the actual position and the target position.

In this document, the term "position" encompasses both the (spatial) position and a (spatial) orientation. A position is for example in relation to a reference object such as a bone structure, a marking device or the operating table. The target position is also a position of structures relative to each other.

The method is particularly preferably suitable for three, four or more bone structures and/or vertebrae. In one advantageous application of the present invention, a profile of the bone structures is described by a multitude of segments, for example the curved profile of vertebrae of a spine.

The three-dimensional dataset is preferably recorded pre-operatively. It is therefore possible to obtain and segment the three-dimensional dataset, which may be complicated, without time restrictions. The three-dimensional dataset is for example obtained by computer tomography (CT) or magnetic resonance tomography (MRT).

In accordance with one embodiment of the invention, the virtual relative position of the segments is changed on the basis of CT-fluoroscopic matching, wherein the positions of the segments are virtually altered with respect to each other, until virtual x-ray recordings of the segments which are correspondingly arranged with respect to each other match the actual x-ray recordings of the bone structures. A virtual x-ray recording is calculated from the position of the segments and the viewing direction from which the x-ray recording is generated.

In an alternative embodiment, the virtual relative position of the segments is changed by scanning landmarks of the bone structures by means of a pointer, and the virtual relative position of the segments is changed such that corresponding landmarks of the segments match the scanned landmarks. This requires less computational power, but presupposes access to the landmarks of the bone structures.

The verification as to whether the virtual relative position of the segments matches a target position of the bone structures is preferably made by assigning each segment of the three-dimensional dataset an individual reference frame and comparing the relative position of the reference frames with a target position of the reference frames. The target position of the reference frames corresponds to the target position of the bone structures. If each segment is fixedly assigned a reference frame, the reference frames of the segments assume their target position with respect to each other, if the segments and therefore the bone structures also assume their target position with respect to each other. The reference frames are for example assigned to the segments directly after the three-dimensional dataset has been segmented or directly before the verification as to whether the virtual relative position of the segments matches a target position of the bone structures.

In one embodiment of the invention, a reference frame consists of a sagittal plane and a coronary plane. If the bone structure is a vertebra of a spine, the sagittal plane is preferably the mid-sagittal plane, which usually represents a horizontal symmetry plane of the vertebra. The coronary plane preferably contains the end points of the transverse processes of the vertebra. The angle between the coronary planes of two adjacent vertebrae defined in this way directly corresponds to the lordosis and/or kyphosis angle. The angle between the mid-sagittal planes of adjacent vertebrae corresponds to the torsion between the two vertebrae. Lordosis and/or kyphosis indicate the curvature of the spine in the sagittal plane.

Alternatively, the reference frame is a coordinate system or a quantity of points, for example characteristic points such as landmarks of the bone structure.

In the case of vertebrae of a spine, the target position of the bone structures is for example defined by determining the lordosis angle and/or kyphosis angle.

When verifying whether the relative position of the bone structures corresponds to the predetermined relative position of the bone structures, a pre-definable deviation is preferably permissible. The two positions are then regarded as being identical even if they deviate from each other, for example within the bounds of the measuring accuracy or medically permissible tolerances.

Optionally, a view of the bone structures in their relative position is calculated from the segments and their virtual relative position, and displayed. The view is for example depicted on a monitor. The surgeon is therefore provided with a representation of the current relative position of the bone structures.

The invention also relates to a program which, when it is loaded onto a data processing device or is running on a data processing device, causes the data processing device to perform one of the methods described above. The program is for example stored on a storage medium or is carried as information by a signal wave. A device in accordance with the invention comprises a computer on which the aforementioned program is run or loaded.

BRIEF DESCRIPTION OF THE DRAWINGS

The present invention shall be described in more detail on the basis of a number of example embodiments.

DETAILED DESCRIPTION

Figure 1:
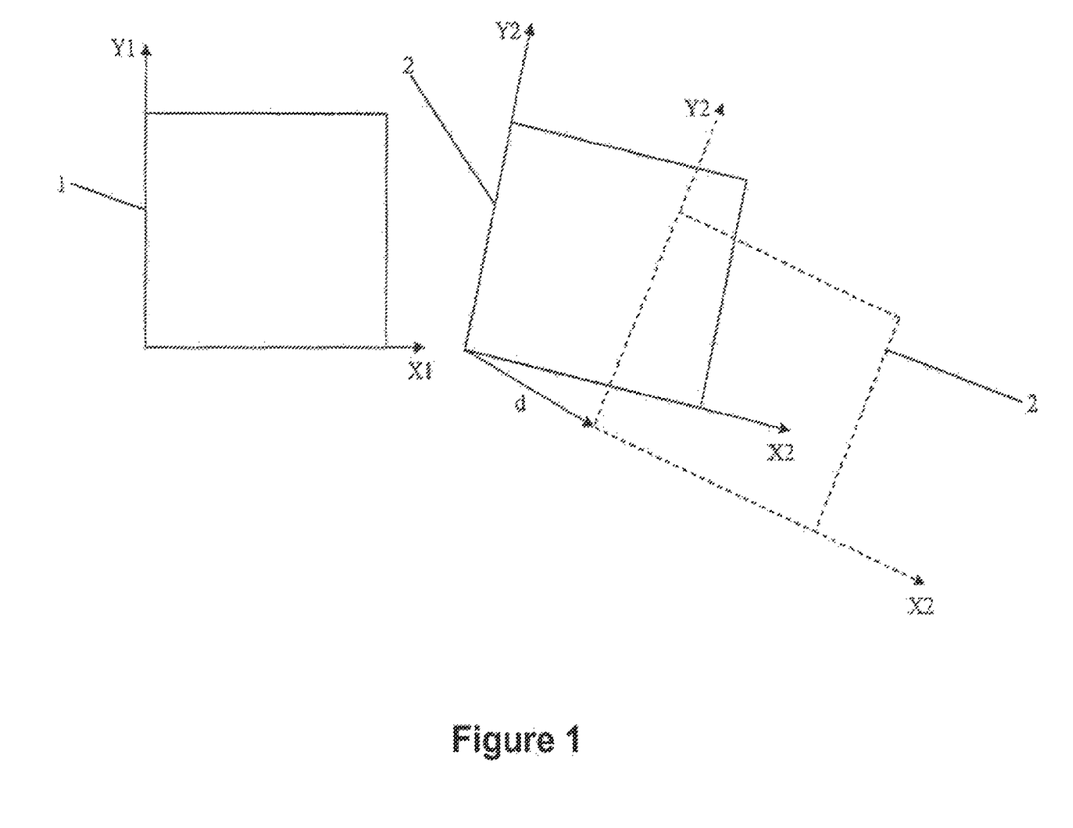
FIG. 1 shows the basic principle of the method, in a two-dimensional representation.

FIG. 1 schematically shows two bone structures 1 and 2, wherein a two-dimensional representation has been chosen in order to illustrate the basic principle of the method. The bone structures 1 and 2 are shown as rectangles, wherein the bone structure 1 serves as the reference. The representation of the bone structure 2 in a continuous line shows it in a first position which has been ascertained by means of a computer tomograph. The reference frame assigned to the bone structure 1 is a Cartesian coordinate system comprising the axes X1 and Y1; the reference frame assigned to the bone structure 2 is a Cartesian coordinate system comprising the axes X2 and Y2. A three-dimensional dataset has been generated with the aid of the computer tomograph and then segmented into two segments. The first segment represents the bone structure 1, and the second segment represents the bone structure 2. The segments serve as a template for subsequently locating the actual relative position of the bone structures. The position of the two reference frames in the three-dimensional dataset is known, since the position of the segments in the three-dimensional dataset is known.

In FIG. 1, the position of the bone structure 2 in relation to the bone structure 1, as registered at a subsequent point in time, is shown in a broken line. As opposed to the position shown in a continuous line, the bone structure 2 has been shifted by the vector d and rotated clockwise by an angle α (not shown in FIG. 1). In order to determine the position of the bone structures, the virtual relative position of the segments is altered such that the virtual relative position of the segments matches the actual relative position of the bone structures. This is for example achieved by successively altering the virtual relative position of the segments and contrasting this position with the actual relative position of the bone structures on the basis of CT-fluoroscopic matching, or by matching scanned landmarks of the bone structures to corresponding landmarks in the segments.

The result is a known alteration in the relative position of the segments, i.e. a shift and/or rotation, relative to the original relative position in the three-dimensional dataset. Since the reference frames are fixedly anchored to the segments, this alteration corresponds to the alteration in the relative position of the reference frames. The current relative position of the reference frames at the time of registration corresponds to the original relative position of the reference frames in the three-dimensional dataset, superimposed with the alteration in the relative position of the reference frames. In order to verify that the relative position of the bone structures matches a target position of the bone structures, the relative position of the reference frames at the time of registration is numerically compared with the target position of the reference frames.

Figure 2:
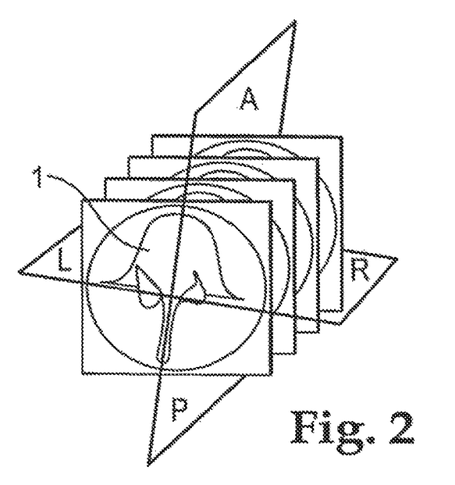
FIG. 2 shows an alternative reference frame.

FIG. 2 shows the use of planes as a reference frame, as an alternative to a (Cartesian) coordinate system. The bone structure 1 is the vertebra of a spine. The planes AP and LR serve as the reference frame. The plane AP is the mid-sagittal plane which passes centrally through the dorsal process. The plane LR is the coronary plane in which the end points of the transverse processes of the vertebra lie. A reference frame defined in this way is particularly advantageous, since the planes directly correspond to medically relevant parameters. Thus, the angle between the LR planes of two adjacent vertebrae corresponds to the lordosis and/or kyphosis angle between the vertebrae.

Figure 3:
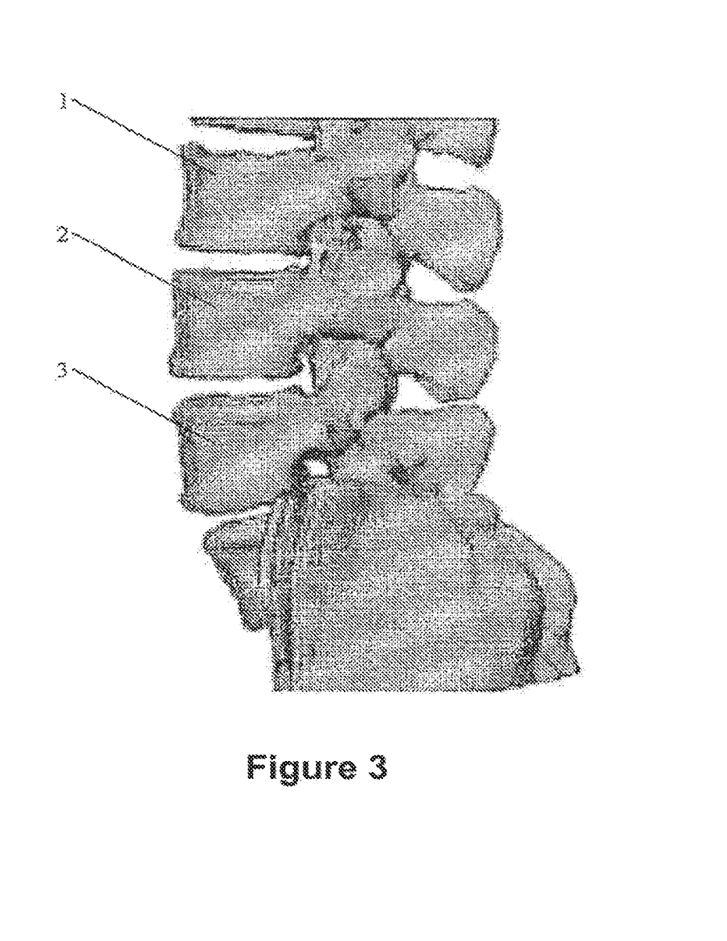
FIG. 3 shows a graphic visualization of a three-dimensional dataset.

FIG. 3 shows a graphic visualization of a three-dimensional dataset which represents a part of a spine. The dataset depicts a spatial density distribution. In the image shown in FIG. 3, the vertebrae 1, 2 and 3 can be seen among other things. The three-dimensional dataset is sub-divided into segments, wherein each segment contains one of the vertebrae. Each of the segments is then assigned an individual reference frame. This is for example achieved automatically on the basis of an analysis of the image dataset, or manually. As described above, a reference frame is a coordinate system or a quantity of planes. The position of the reference frames with respect to each other represents the position of the vertebrae with respect to each other at the time of recording the three-dimensional dataset. The relative position of the reference frames is known, since the relative position of the segments in the three-dimensional dataset is known.

Figure 4A:
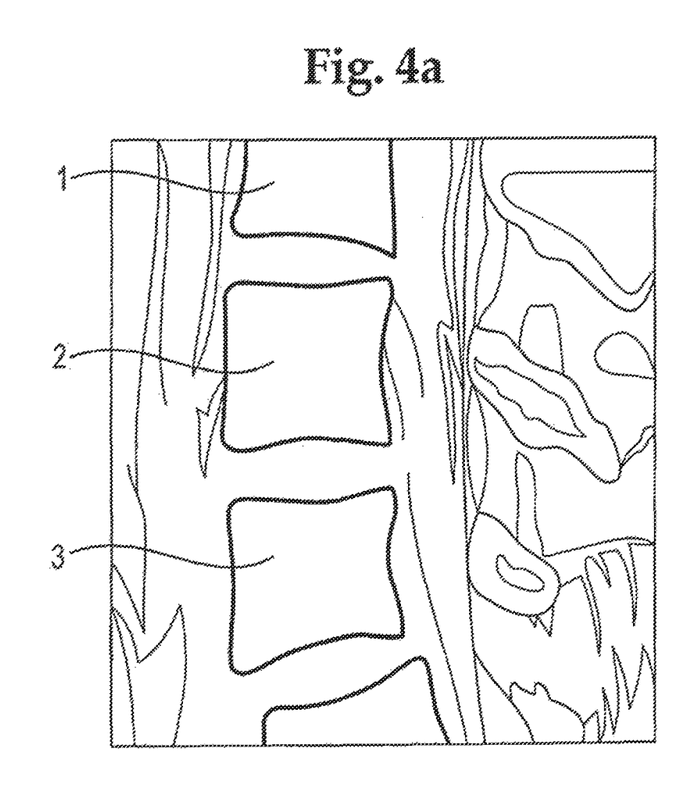
FIGS. 4A and 4B show two x-ray recordings.
Figure 4B:
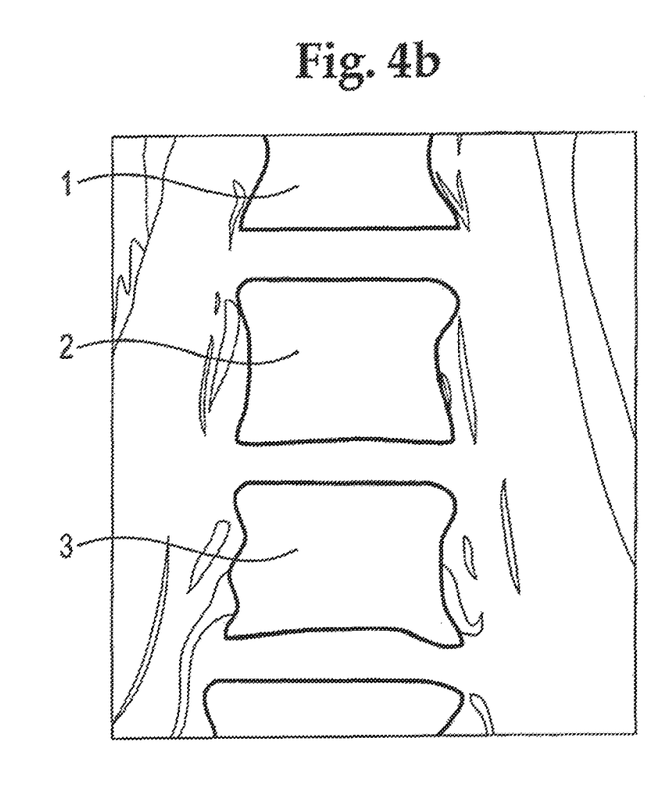

In a subsequent step, the actual position of the vertebrae 1, 2 and 3 at a subsequent point in time is determined—in the present example, on the basis of CT-fluoroscopic matching. To this end, two-dimensional x-ray images are recorded, such as are shown in FIGS. 4A and 4B. FIG. 4A shows an x-ray recording taken from the side, and FIG. 4B shows an x-ray recording of the part of the spine from FIG. 3, taken from the front.

Change-in-position data of the segments is calculated from the two x-ray recordings and the segmented three-dimensional dataset, wherein the segments of the three-dimensional dataset are virtually shifted and/or rotated relative to each other in steps. Virtual x-ray images are then calculated from the new arrangement of the segments in each step. If these virtual x-ray images match the recorded x-ray images, then the virtual position of the segments corresponds to the actual position of the vertebrae. The changes in the positions of the segments relative to their position in the original three-dimensional dataset are combined to form the change-in-position data. The position of the reference frames relative to each other at the time of recording the x-ray images, i.e. at the time of registration, then corresponds to superimposing the relative position of the reference frames when the three-dimensional dataset is recorded with the change-in-position data.

Optionally, a three-dimensional representation of the current status of the spine is generated from the relative position of the vertebrae, analogous to the representation from FIG. 3. This representation serves as a visual feedback for the surgeon regarding the current relative position of the vertebrae.

Figure 5:
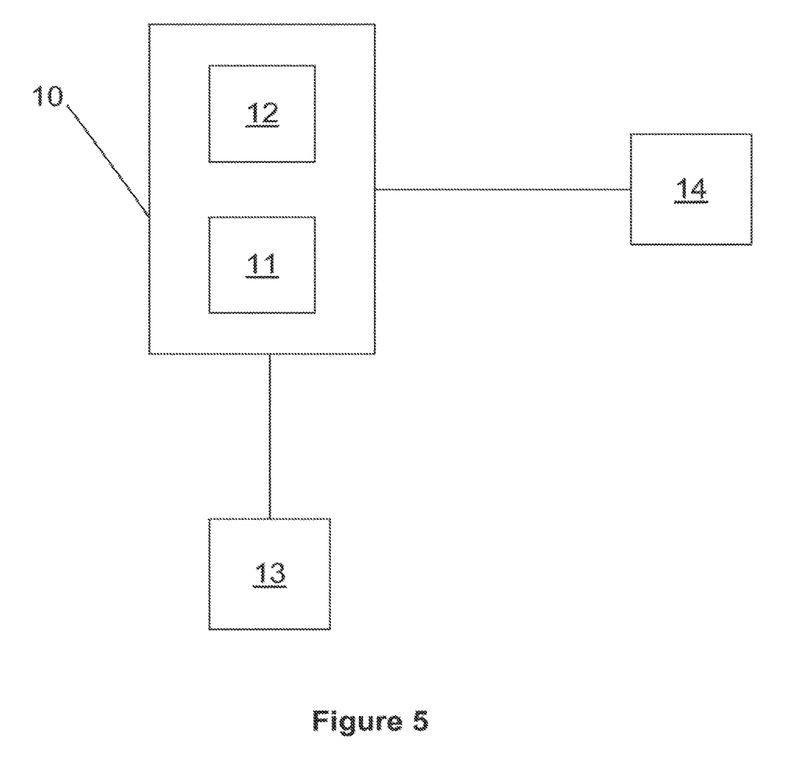
FIG. 5 shows a device for performing the method.

FIG. 5 schematically shows a device for determining the relative position of bone structures. The device comprises a computer 10 which contains among other things a memory 11 and a computational unit 12. A computer tomograph 13 and an x-ray apparatus 14 are connected to the computer 10. The computer tomograph 13 generates the three-dimensional dataset, which is stored in the memory 11 of the computer 10. To this end, a direct connection can exist between the computer tomograph 13 and the computer 10. Alternatively, the data is transferred from the computer tomograph 13 into the memory 11 via a network or with the aid of a data carrier. The three-dimensional dataset is segmented in the computer tomograph 13 or in the computer 10.

The x-ray apparatus 14 generates x-ray images which contain information on the position of the bone structures. These x-ray images are transferred to the computer 10, where they are evaluated by the computational unit 12. The computational unit 12 calculates the change-in-position data of the segments and the relative position of the bone structures and compares them with a target position. An output device, for example a monitor, for depicting a representation of the bone structures in their relative position at the time of recording the x-ray images is not shown in FIG. 5.

Figure 6:
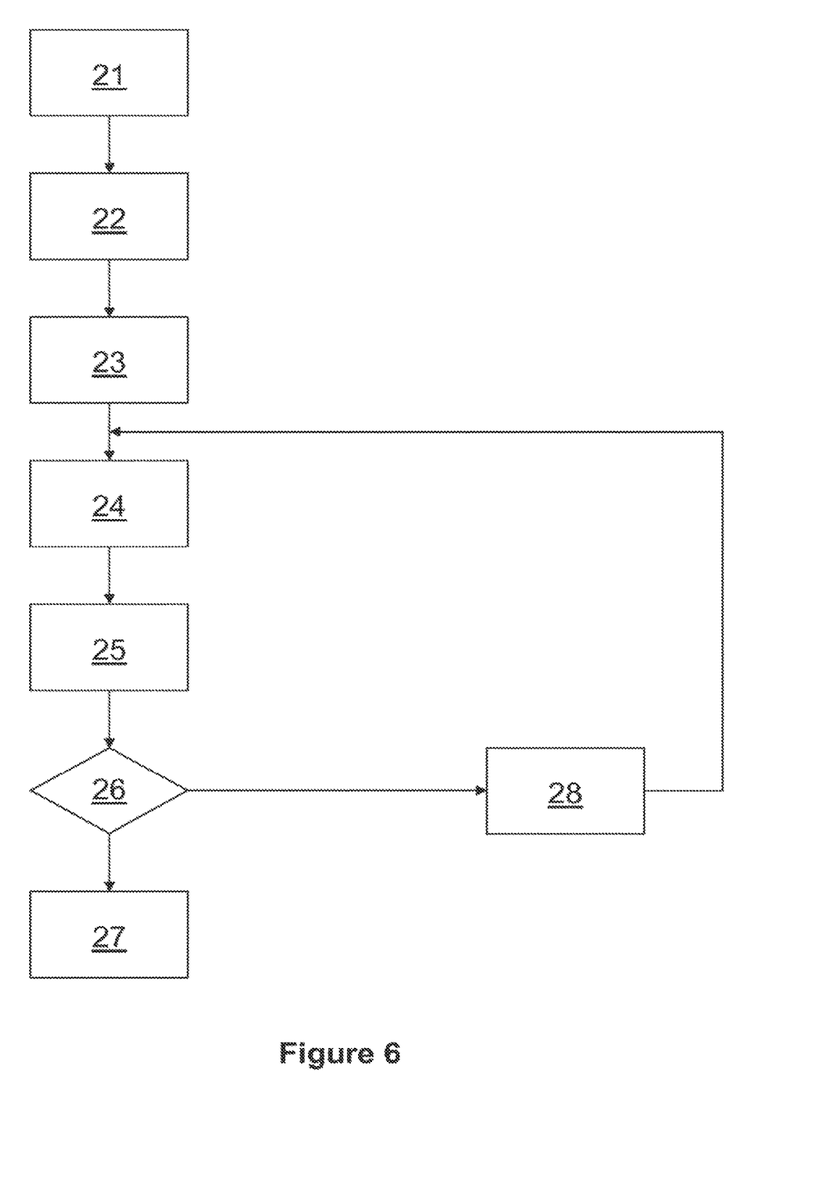
FIG. 6 shows a flow diagram for a method for verifying the relative position of bone structures.

FIG. 6 shows a flow diagram of a method for verifying the relative position of bone structures, wherein in a first step 21, a pre-operative scan of the bone structures is performed and a three-dimensional dataset is generated. In step 22, the three-dimensional dataset is segmented into segments which each represent a bone structure. In step 23, each of the segments is assigned an individual reference frame. In step 24, the positions of the bone structures are intra-operatively determined with the aid of CT-fluoroscopic matching, as described above. This results in change-in-position data from which the relative position of the reference frames at the time of recording the x-ray images is calculated, taking into account the position of the reference frames in the three-dimensional dataset. Additionally or alternatively, the positions of the bone structures can be determined in step 24 by means of so-called pointers. The pointers comprise detectable markers, the position of which is known with respect to the pointer tip. The pointer tip is in particular brought into contact with landmarks of the bone structures.

In step 25, a view of the bone structures in their relative position is calculated from the segments and their virtual position, and displayed.

In step 26, a verification is made as to whether the position of the reference frames relative to each other corresponds to a determined target position, wherein a tolerance is optionally permissible. If the relative position corresponds to the target position, a corresponding signal is output in step 27.

If the relative position does not correspond to the target position, then the position of the patient and thus the relative position of the bone structures is altered in step 28. The method is then continued from step 24.

One or more of the bone structures are optionally provided with marking devices, for example marker stars. A marker star is a three-dimensional arrangement of three or more spheres, the position of which can be ascertained with the aid of a detection device such as a 3D camera. Due to the fixed connection between the marking device and the marked structure, it is thus possible to deduce the position of the structure. The position of the marked bone structure can be determined with the aid of the marker device. In particular, notifying information (for example, a display on a screen, audio, etc.) can be output which provides information on the position. If the position of the bone structures which are provided with marking devices is also calculated on the basis of the method described above, then the marking devices can be used to check the method, by comparing the measured position of the marked bone structures with the calculated position.

Instead of by means of computer tomography, the three-dimensional dataset can also be recorded using any other three-dimensionally imaging method, for example by using a magnetic resonance tomograph.

Computer program elements of the invention may be embodied in hardware and/or software (including firmware, resident software, micro-code, etc.). The computer program elements of the invention may take the form of a computer program product which may be embodied by a computer-usable or computer-readable storage medium comprising computer-usable or computer-readable program instructions, "code" or a "computer program" embodied in said medium for use by or in connection with the instruction executing system. Within the context of this application, a computer-usable or computer-readable medium may be any medium which can contain, store, communicate, propagate or transport the program for use by or in connection with the instruction executing system, apparatus or device. The computer-usable or computer-readable medium may for example be, but is not limited to, an electronic, magnetic, optical, electromagnetic, infrared or semiconductor system, apparatus, device or medium of propagation, such as for example the Internet. The computer-usable or computer-readable medium could even for example be paper or another suitable medium on which the program is printed, since the program could be electronically captured, for example by optically scanning the paper or other suitable medium, and then compiled, interpreted or otherwise processed in a suitable manner. The computer program product and any software and/or hardware described here form the various means for performing the functions of the invention in the example embodiment(s).

Although the invention has been shown and described with respect to one or more particular preferred embodiments, it is clear that equivalent amendments or modifications will occur to the person skilled in the art when reading and interpreting the text and enclosed drawing(s) of this specification. In particular with regard to the various functions performed by the elements (components, assemblies, devices, compositions, etc.) described above, the terms used to describe such elements (including any reference to a "means") are intended, unless expressly indicated otherwise, to correspond to any element which performs the specified function of the element described, i.e. which is functionally equivalent to it, even if it is not structurally equivalent to the disclosed structure which performs the function in the example embodiment(s) illustrated here. Moreover, while a particular feature of the invention may have been described above with respect to only one or some of the embodiments illustrated, such a feature may also be combined with one or more other features of the other embodiments, in any way such as may be desirable or advantageous for any given application of the invention.

What is claimed is:

1. A method for verifying a relative position between at least two bone structures in an associated patient, the method comprising:
    recording a three-dimensional dataset which represents a relative position between the at least two bone structures;
    segmenting the three-dimensional dataset into at least two virtual segments, wherein each virtual segment comprises a three-dimensional representation of a respective bone structure of the at least two bone structures, and the at least two virtual segments exhibit a virtual fixed relative position between each other in the three-dimensional dataset;
    registering the at least two virtual segments with the at least two bone structures by virtually selectively shifting and/or rotating, using a computational unit, a position of each of the at least two virtual segments to obtain a virtual registered relative position between the virtual segments such that the virtual registered relative position between each of the virtual segments matches an actual relative position between each of the at least two bone structures in an associated patient;
    determining change-in-position data representative of an amount of the shifting and/or rotating selectively performed in the registering for matching the virtual registered relative position between each of the virtual segments with the actual relative position between each of the at least two bone structures in an associated patient; and
    verifying the relative position between the at least two bone structures by determining, based on the change-in-position data, whether the virtual registered relative position of the virtual segments after the registering matches a target relative position of the at least two bone structures.

2. The method according to claim 1, wherein the at least two bone structures are at least two vertebrae of a spine.

3. The method according to claim 1, wherein virtually changing the position of the segments relative to each other such that the virtual relative position of the segments matches an actual position of the bone structures comprises changing the virtual relative position of the segments based on CT-fluoroscopic matching.

4. The method according to claim 1 wherein virtually changing the position of the segments relative to each other such that the virtual relative position of the segments matches an actual position of the bone structures comprises scanning landmarks of the bone structures by means of a pointer, and virtually changing the position of the segments relative to each other until corresponding landmarks of the segments match the scanned landmarks.

5. The method according to claim 1, wherein the recording a three-dimensional dataset comprises recording the three-dimensional dataset preoperatively.

6. The method according to claim 1, wherein the verifying comprises assigning each segment of the three-dimensional dataset an individual reference frame and comparing a relative position of each reference frame with a target relative position of each reference frame which corresponds to the target relative position of the bone structures.

7. The method according to claim 6, wherein each reference frame consists of a sagittal plane and a coronal plane.

8. The method according to claim 1, further comprising defining the target relative position of the bone structures by determining at least one of a lordosis angle, kyphosis angle, a translation in the media-lateral direction or a translation in the anterior-posterior direction.

9. The method according to claim 1, wherein verifying includes permitting a pre-definable deviation between the virtual relative position of the segments and the target relative position of the bone structures.

10. The method according to claim 1, further comprising:
    calculating a view of the bone structures in their actual relative position, said calculation based on the segments and their virtual relative position; and
    displaying the calculated view of the bone structures.

11. A computer readable medium comprising computer executable instructions adapted to perform the method in accordance with claim 1.

12. The method according to claim 1, further comprising outputting a result of the verification on an output device.

13. A computer system, comprising:
    a processor;
    a memory operatively coupled to the processor; and
    logic which executes in the processor from the memory and which, when executed by the processor, causes the computer to verify a relative position between at least two bone structures in an associated patient by:
        recording a three-dimensional dataset which represents a relative position between the at least two bone structures;
        segmenting the three-dimensional dataset into at least two virtual segments, wherein each virtual segment comprises a three-dimensional representation of a respective bone structure of the at least two bone structures, and the at least two virtual segments exhibit a virtual fixed relative position between each other in the three-dimensional dataset;

registering the at least two virtual segments with the at least two bone structures by virtually selectively shifting and/or rotating a position of each of the at least two virtual segments to obtain a virtual registered relative position between each of the virtual segments such that the virtual registered relative position between each of the virtual segments matches an actual relative position between each of the at least two bone structures in an associated patient;

determining change-in-position data representative of an amount of the shifting and/or rotating selectively performed in the registering for matching the virtual registered relative position between each of the virtual segments with the actual relative position between each of the at least two bone structures in an associated patient; and verifying the relative position between the at least two bone structures by determining, based on the change-in-position data, whether the virtual registered relative position of the virtual segments after the registering matches a target relative position of the at least two bone structures.

14. A method for verifying a relative position between at least two bone structures in an associated patient, the method comprising:

obtaining a three-dimensional dataset that represents a relative position between the at least two bone structures;

segmenting the three-dimensional dataset into a plurality of virtual segments, wherein each virtual segment of the plurality of virtual segments represents a bone structure of the at least two bone structures, and each segment of the plurality of virtual segments exhibits a virtual fixed relative position between other segments in the three-dimensional dataset;

determining an actual relative position between the at least two bone structures;

registering the at least two bone structures with the plurality of virtual segments by virtually selectively shifting and/or rotating a position of each of the plurality of virtual segments to obtain a virtual registered relative position between the virtual segments such that the virtual registered position of the segments matches the actual relative position between each of the at least two bone structures;

determining change-in-position data representative of an amount of the shifting and/or rotating selectively performed in the registering for matching the virtual registered relative position between each of the plurality of virtual segments with the actual relative position between each of the at least two bone structures in an associated patient; and after the registering and based on the change-in-position data, comparing the matched position to a target relative position of the at least two bone structures; and outputting a result of the comparison.

* * * * *